US008740788B1

(12) United States Patent
Mettler, Jr.

(10) Patent No.: US 8,740,788 B1
(45) Date of Patent: *Jun. 3, 2014

(54) TONGUE RETRACTION METHOD AND APPARATUS WITH RELIEF NOTCH

(75) Inventor: Gilbert William Mettler, Jr., Washington, NH (US)

(73) Assignee: Gil Mettler, Washington, NH (US)

( * ) Notice: Subject to any disclaimer, the term of this patent is extended or adjusted under 35 U.S.C. 154(b) by 343 days.

This patent is subject to a terminal disclaimer.

(21) Appl. No.: 12/794,686

(22) Filed: Jun. 4, 2010

(51) Int. Cl.
*A61B 13/00* (2006.01)
*A61B 17/24* (2006.01)

(52) U.S. Cl.
USPC .......................................... 600/240; 606/161

(58) Field of Classification Search
USPC ................. D24/136; 600/184, 201, 235, 237, 600/240–241; 606/161
See application file for complete search history.

(56) References Cited

U.S. PATENT DOCUMENTS

| 118,386 | A | | 8/1871 | Osborn |
| 412,409 | A | | 10/1889 | Osborne |
| 477,791 | A | | 6/1892 | Andrews |
| 883,106 | A | | 3/1908 | Galloway |
| 1,042,133 | A | | 10/1912 | Marshall |
| 1,187,079 | A | * | 6/1916 | Miller et al. ................. 600/240 |
| 2,218,072 | A | | 10/1940 | Runnels |
| 2,491,274 | A | | 12/1949 | McNeill |
| 2,543,999 | A | | 3/1951 | Voss |
| 2,583,750 | A | | 1/1952 | Runnels |
| 2,653,597 | A | | 9/1953 | Canan |
| 2,723,661 | A | | 11/1955 | Hull |
| 3,768,477 | A | | 10/1973 | Anders et al. |
| 3,863,627 | A | | 2/1975 | Bouffard |
| 3,890,960 | A | * | 6/1975 | Wunsch et al. ................. 600/191 |
| 3,943,592 | A | | 3/1976 | Bhaskar et al. |
| D243,422 | S | | 2/1977 | Varga |
| 4,079,478 | A | | 3/1978 | Andrews |
| D263,743 | S | | 4/1982 | Priestman |

(Continued)

FOREIGN PATENT DOCUMENTS

| EP | 1034721 A1 | 9/2000 |
| WO | WO-2009091529 A2 | 7/2009 |
| WO | WO-2009091529 A3 | 7/2009 |

OTHER PUBLICATIONS

"U.S. Appl. No. 12/031,911, Response filed Sep. 29, 2011 to Final Office Action mailed Jun. 2, 2011", 15 pgs.

(Continued)

*Primary Examiner* — Nicholas Woodall
*Assistant Examiner* — Larry E Waggle, Jr.
(74) *Attorney, Agent, or Firm* — Schwegman, Lundberg & Woessner, P.A.

(57) ABSTRACT

Some embodiments includes an apparatus for retracting an animal tongue that includes a handle that is elongate and that includes a proximal portion and a distal portion and a tongue retraction cup coupled to the distal portion of the handle, the tongue retraction cup being generally concave and sized such that a first side of the tongue retraction cup extends over a first side of the tongue, a second side opposite the first side extends over a second side of the tongue that is opposite the first side of the tongue, a dorsal portion of the cup extends along the dorsal portion of the tongue and a posterior extending tip extends at least partially along the back of the tongue, the first side, second side, and posterior extending tip defining a tongue receiving cavity of the tongue retraction cup.

13 Claims, 13 Drawing Sheets

(56) References Cited

U.S. PATENT DOCUMENTS

| | | | |
|---|---|---|---|
| 4,455,704 A | 6/1984 | Williams | |
| 4,589,848 A | 5/1986 | Inoue | |
| 4,638,521 A | 1/1987 | Potente et al. | |
| D305,797 S | 1/1990 | Robinson et al. | |
| D309,528 S | 7/1990 | Valenti | |
| D317,821 S * | 6/1991 | Aoyagi | D24/136 |
| 5,176,151 A | 1/1993 | Harding | |
| 5,226,197 A | 7/1993 | Nack et al. | |
| D344,335 S | 2/1994 | Elisha | |
| D359,556 S | 6/1995 | Hale et al. | |
| 5,518,503 A | 5/1996 | Rooney et al. | |
| 5,553,627 A | 9/1996 | Newkirk | |
| 5,656,014 A | 8/1997 | Rooney et al. | |
| D391,370 S | 2/1998 | Cho | |
| 5,730,597 A | 3/1998 | Luttrell | |
| 5,735,864 A | 4/1998 | Heisinger, Jr. | |
| 5,774,925 A | 7/1998 | Pryor, III et al. | |
| 5,779,654 A | 7/1998 | Foley et al. | |
| 5,810,856 A | 9/1998 | Tveras | |
| 5,817,114 A | 10/1998 | Anderson et al. | |
| D406,891 S | 3/1999 | Smith | |
| 5,893,860 A | 4/1999 | Ripich et al. | |
| 5,897,492 A | 4/1999 | Feller et al. | |
| 5,910,151 A | 6/1999 | Adedokun | |
| 5,984,935 A | 11/1999 | Welt et al. | |
| 6,015,293 A | 1/2000 | Rimkus | |
| 6,045,499 A | 4/2000 | Pitesky | |
| 6,083,235 A | 7/2000 | Wagner | |
| D433,134 S | 10/2000 | Pitesky | |
| 6,142,777 A | 11/2000 | Winston et al. | |
| 6,352,545 B1 | 3/2002 | Wagner | |
| 6,440,149 B1 | 8/2002 | Potti | |
| 6,520,953 B1 | 2/2003 | Schultz | |
| D471,276 S | 3/2003 | Potti | |
| 6,655,960 B2 | 12/2003 | Fischer | |
| D484,978 S | 1/2004 | Syal | |
| D502,263 S | 2/2005 | Feller et al. | |
| 6,921,409 B2 | 7/2005 | Richard | |
| D523,299 S | 6/2006 | Johnson | |
| D536,452 S | 2/2007 | Geiberger et al. | |
| D545,445 S | 6/2007 | Klein | |
| D574,494 S | 8/2008 | Schmitt | |
| D594,122 S | 6/2009 | Mettler | |
| 2002/0128673 A1 | 9/2002 | Ripich et al. | |
| 2004/0152031 A1 | 8/2004 | Takahashi | |
| 2006/0025791 A1 | 2/2006 | Ripich et al. | |
| 2006/0036133 A1 | 2/2006 | Demsky | |
| 2007/0163064 A1 | 7/2007 | Wong et al. | |
| 2008/0045988 A1 | 2/2008 | Abbott et al. | |
| 2008/0154291 A1 | 6/2008 | Bosma et al. | |
| 2008/0208228 A1 | 8/2008 | Mueller | |
| 2009/0111069 A1 | 4/2009 | Wagner | |
| 2009/0182364 A1 * | 7/2009 | Mettler, Jr. | 606/161 |

OTHER PUBLICATIONS

"U.S. Appl. No. 12/013,911, Final Office Action mailed Jul. 3, 2010", 12 pgs.

"U.S. Appl. No. 12/013,911, Examiner Interview Summary mailed May 10, 2012", 3 pgs.

"U.S. Appl. No. 12/013,911, Final Office Action mailed Jun. 2, 2011", 20 pgs.

"U.S. Appl. No. 12/013,911, Non Final Office Action mailed Jan. 30, 2012", 25 pgs.

"U.S. Appl. No. 12/013,911, Non Final Office Action mailed Mar. 4, 2011", 13 pgs.

"U.S. Appl. No. 12/013,911, Response filed Mar. 15, 2011 to Non-Final Office Action mailed Mar. 4, 2011", 15 pgs.

"U.S. Appl. No. 12/013,911, Response filed Apr. 30, 2012 to Non Final Office Action mailed Jan. 30, 2012", 19 pgs.

"U.S. Appl. No. 12/013,911, Response filed Dec. 13, 2010 to Final Office Action mailed Jul. 13, 2010", 14 pgs.

"U.S. Appl. No. 12/013,911, Response filed Jun. 4, 2010 to Non Final Office Action mailed Mar. 16, 2010", 15 pgs.

Glazer, H.S., "What's Hot and What's Getting Hotter", *AGD Impact*, (Sep. 2012), 20-21.

"U.S. Appl. No. 12/013,911 Restriction Requirement Received Oct. 6, 2009", 6.

"U.S. Appl. No. 12/013,911 Restriction Requirement Response filed Dec. 7, 2009", 8.

"U.S. Appl. No. 12/013,911, Non-Final Office Action mailed Mar. 16, 2010", 12.

"U.S. Appl. No. 29/302,281, Non-Final Office Action mailed Sep. 16, 2008", 11 pgs.

"U.S. Appl. No. 29/302,281, Notice of Allowance mailed Jan. 28, 2009", 6 pgs.

"U.S. Appl. No. 29/302,281, Response filed Dec. 15, 2008 to Non-Final Office Action mailed Sep. 16, 2008", 7 pgs.

"U.S. Appl. No. 12/013,911 Restriction Requirement mailed Nov. 5, 2009", 7 Pgs.

"International Application Serial No. PCT/US2009/000198, Search Report mailed Jul. 27, 2009", 4 pgs.

"International Application Serial No. PCT/US2009/000198, Written Opinion mailed Jul. 27, 2009", 4 pgs.

European Application Serial No. 09702805.4, Response filed Feb. 14, 2013 to Extended European Search Report mailed Jul. 27, 2012, 14 pgs.

European Application Serial No. 09702805.4, Supplementary European Search Report mailed Jul. 27, 2012 7 pgs.

International Application Serial No. PCT/US2009/000198, International Preliminary Report on Patentability dated Jul. 20, 2010, 5 pgs.

* cited by examiner

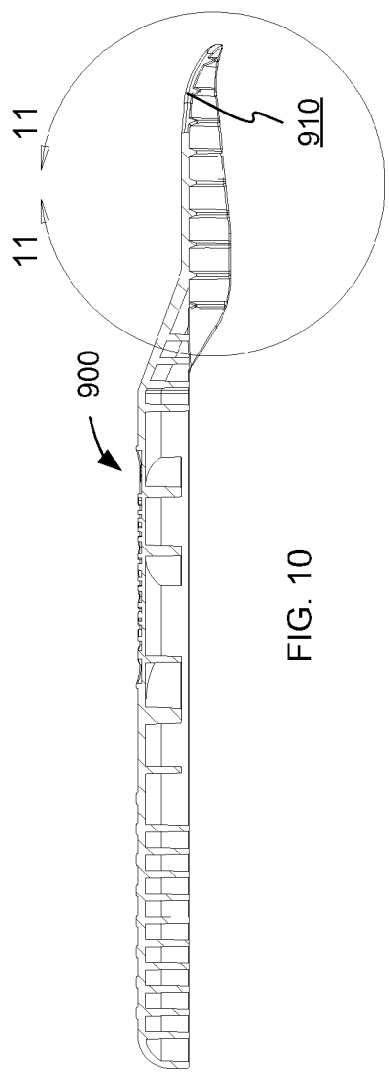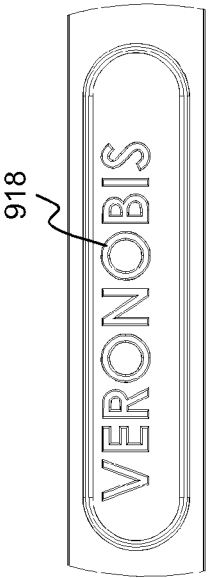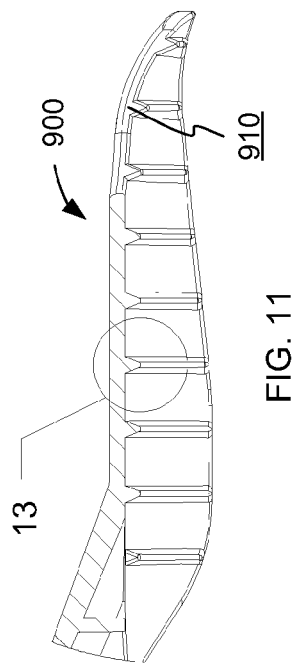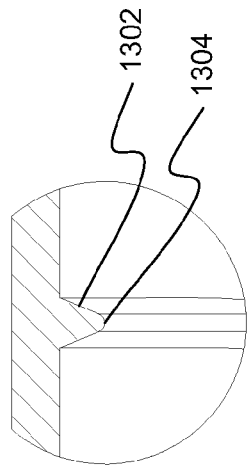
FIG. 10
FIG. 12
FIG. 11
FIG. 13

TONGUE RETRACTION METHOD AND APPARATUS WITH RELIEF NOTCH

TECHNICAL FIELD

Various embodiments described herein relate generally to oral tools, including a tongue retraction and cleaning method and apparatus.

BACKGROUND

Care providers need to manage the location of the tongue during examination and treatment of patients. Accordingly, apparatus, system and method are needed to provide these benefits, among others. In some instances, apparatus and method capable of positioning the tongue while reducing or eliminating contact with the tongue are desired.

BRIEF DESCRIPTION OF THE DRAWINGS

FIG. 10 is a cross sectioned view taken along line 10-10 in FIG. 9A.

FIG. 11 is a sectioned view taken along section 11-11 in FIG. 9A, showing an indicia optionally disposed on a tongue retractor, according to some embodiments.

FIG. 12 is a sectioned close up view taken along section 12-12 in FIG. 10.

FIG. 13 is a sectioned view taken along section 13-13 in FIG. 12, showing an optional cleaning element disposed on a receiving cup of a tongue retractor, according to some embodiments.

DETAILED DESCRIPTION

This describes embodiments of a tongue retractor and shows examples of the tongue retractor in use. Among the tongue retractors discussed here are embodiment that have a notch sized to allow the tongue retractor to be used under the tongue with the tongue's frenulum placed into a notch or relief in the tongue retractor. An oral frenulum is a fold of tissue that secures or restricts the motion of a mobile organ. There is an oral frenulum under the tongue connecting the tongue to the floor of the mouth. Some examples discussed here have a notch to so that the tongue retractor can be extended under the tongue in a dorsal direction without being restricted by the oral frenulum. In use, the tongue retractor applies pressure to the tongue along an anterior or cranial direction to move the tongue so that diagnosis or treatment procedures occurring under the tongue are made easier.

Figure 2:
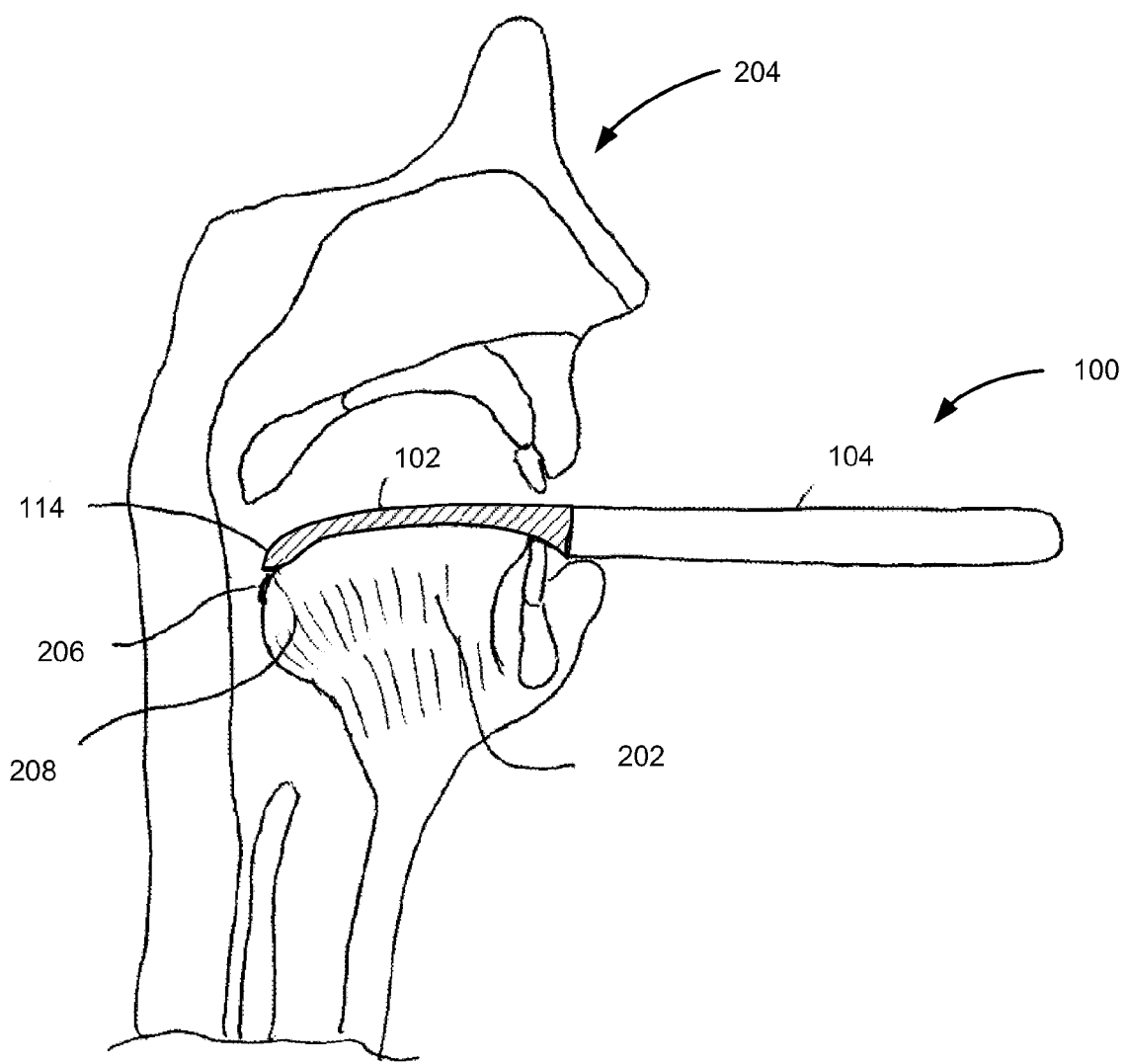
FIG. 2 illustrates a human and a partial cross section of a tongue retractor taken along line 2-2 in FIG. 1.

Although these figures are directed toward a tongue retractor, embodiments that additionally clean the tongue are contemplated, as disclosed herein. In various embodiments, the tongue retractor 100 includes a tongue receiving or retraction cup 102 for cupping and retracting a tongue via force applied using the handle 104. In various examples, the tongue retraction handle 104 is adapted to force the tongue retraction cup 102 to forcibly retract the animal tongue one or more of the anterior-posterior axis, the dorsal-ventral axis, and the right-left axis, as well as long combinations of these axes. The tongue receiving cup 102 is coupled to the handle 104. Various coupling means are possible, including, but not limited to, molding, welding, adhesive, and the like. In some examples, a cup and the handle are part of a continuous mold. A partial cross section of the tongue retractor 100 as applied to the tongue 202 of an animal 204 is illustrated in FIG. 2, according to some embodiments.

The present subject matter is effective on animals. Animals contemplated include, but are not limited to, humans, canines and felines. The present subject matter is for use by various care providers, including medical doctors and associated care providers, dentists and associated care providers and veterinary doctors and associated care providers. Consumers additionally are able to purchase devices disclosed herein over the shelf and apply them to one or more animals such as humans or other animals. Dental procedures contemplated include, but are not limited to, titanium spray, computer aid design rendering, computer aided machining, surgery and tooth reconstruction, as well as various hygienist procedures.

In various embodiments, the devices disclosed herein are sized for use on a particular animal. For example, in some embodiments, the present subject matter is sized for use with humans. In additional embodiments, the present subject matter is sized for use with other animals. Embodiments that are sized for use on multiple animals are additionally contemplated. Further, embodiments that are sized for an animal at a particular stage of growth (e.g., an infant stage, an adult stage, etc.) are contemplated.

The embodiments disclosed herein include several size variables that are sized to fit a particular animal. FIG. 2 illustrates a human and a partial cross section of a tongue retractor taken along line 2-2 in FIG. 1. The tongue retractor 100 provides a means for cupping the tongue. Means for cupping the tongue comprise any of the devices described herein that contact at least a dorsal portion of the tongue. In some embodiments, the tongue retractor 100 provides a means for cupping the tongue without extending over circumvallate papillae of the tongue 202 when the tongue receiving cup 102 is mated to the tongue. In additional embodiments, the tongue receiving cup 102 extends over the circumvallate papillae 206. The example illustrated in FIG. 2 demonstrates a tongue retractor 100 that includes a tongue receiving cup 102 cross sectioned at an anterior posterior dorsal ventral plane, also known as a sagittal plane, and that has a form factor that substantially matches across section of the tongue 202 cross sectioned at the anterior posterior dorsal ventral plane. In some embodiments, the form factor does not extend around the tip of the tongue. Embodiments which extend around the tip of the tongue, such as by extending between the tongue 202 and one or more teeth such as incisors of the animal, are contemplated.

Figure 1:
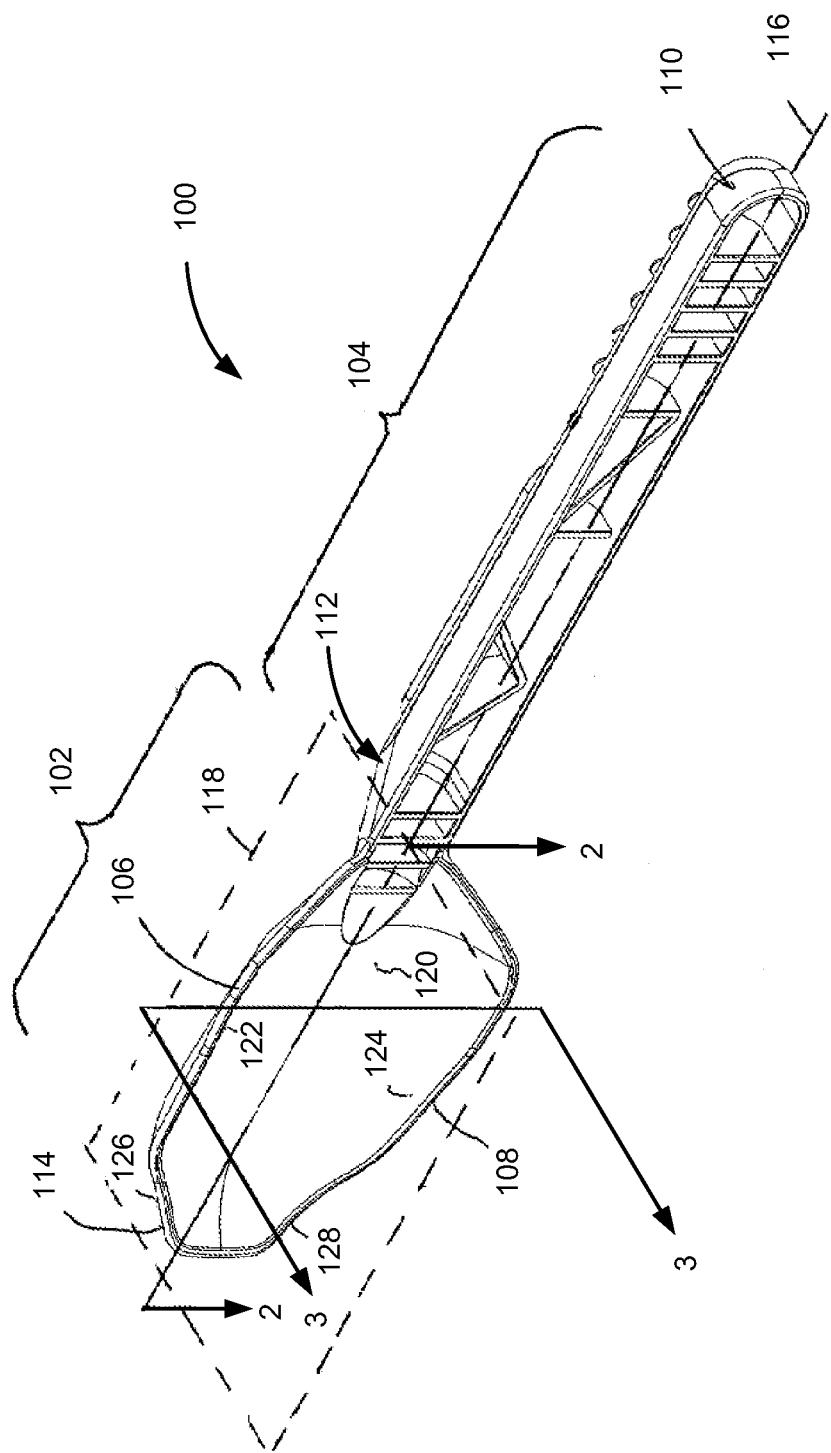
FIG. 1 illustrates a perspective view of a tongue retractor, according to some embodiments.
Figure 3:
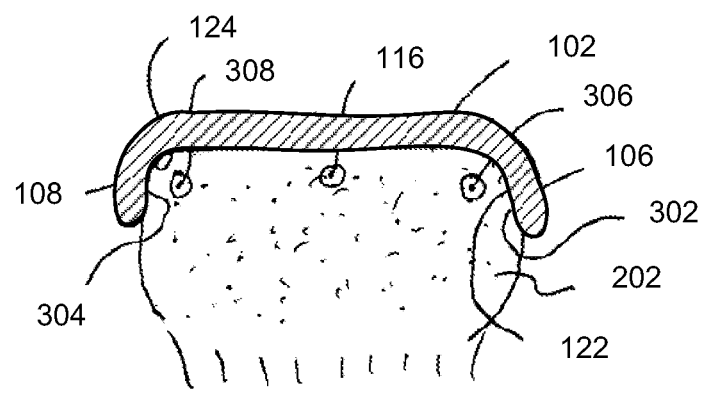
FIG. 3 illustrates a human and a partial cross section of a tongue retractor taken along line 3-3 in FIG. 1.

FIG. 3 illustrates a human and a partial cross section of a tongue retractor taken along line 3-3 in FIG. 1. Although a tongue retractor is disclosed in the illustration, embodiments that additionally adapted to clean the tongue are contemplated, as disclosed herein. In the illustration, the tongue retractor 100 defines a cross section of the tongue receiving cup 102 at a left right dorsal ventral plane, also known as a coronal plane, that has a form factor that substantially matches a cross section of the tongue 202 at the left right dorsal ventral plane of the animal to which the tongue retractor 100 is being applied to.

Returning to the embodiment of FIG. 1, the handle 104 is elongate comprising a proximal portion 110 and a distal portion 112. The tongue retractor includes a tongue receiving cup 102 coupled to the distal portion 112 of the handle 104. In various embodiments, the tongue receiving cup 102 is generally concave. In the embodiment illustrated in FIG. 3, the tongue receiving cup 102 is sized such that a first side 106 of the tongue receiving cup 102 extends at least partially over a first lateral side 302 of the tongue 202. The tongue receiving cup 102 illustrated additionally extends at least at least partially over a second lateral side 304 of the tongue 202 that is opposite the first lateral side 302 of the tongue 202. The tongue receiving cup 102 additionally extends over a dorsal portion of the tongue. In some embodiments this includes only the oral portion of the tongue. In additional embodiments, this includes the back of the tongue, also referred to as the oral pharyngeal portion of the tongue. As illustrated in FIG. 2, the tongue receiving cup 102 includes a tip 114 that extends at least partially along the back 208 of the tongue 202 toward and along the oral pharyngeal portion of the tongue. In various embodiments, the first side 106, second side 108, and the tip 114 define a tongue receiving cavity of the tongue receiving cup 102.

The perspective view of FIG. 1 illustrates a major axis 116. A proximal portion 110 is located at a first end of the major axis 116 and the distal portion 112 is located opposite the proximal portion in a distal direction along the major axis 116. The tongue receiving cup 102 is coupled to the handle 104 at the distal portion 112 of the handle. In various embodiments, the tongue receiving cup 102 is bisected by a major plane 118 along the major axis 116. The tongue receiving cup 102 is one of several shapes contemplated, and other shapes, including irregular shapes, are possible without departing from the present subject matter.

Figure 4:
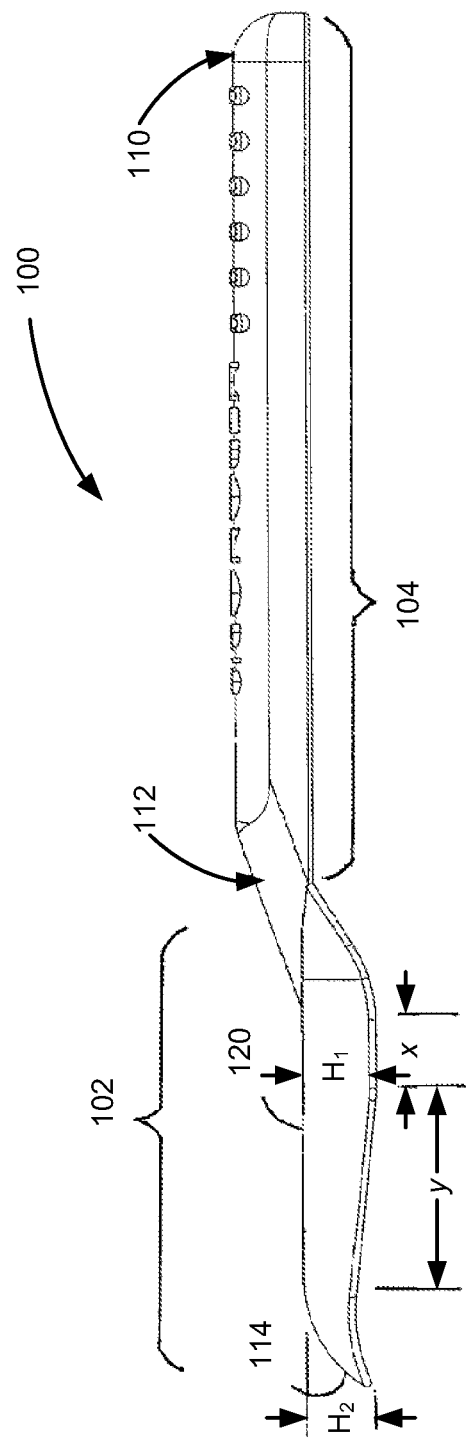
FIG. 4 illustrates a side view of a tongue retractor, according to some embodiments.

In various embodiments, the tongue receiving cup 102 includes a base 120 that is generally planar, with the base being perpendicular to the major plane 118. The base 120 is at least partially disposed along a dorsal surface of the tongue in various embodiments. The first side 106 of the tongue receiving cup 102 includes a first wall 122 curving away from the base 120 in a direction away from the major plane 118, the first wall 122 curving around a first wall axis 306, illustrated in FIG. 3, that is parallel to the major axis 116. A second wall 124 opposite the first wall 122 is illustrated, with the second wall curving away from the base 120 in a direction away from the major plane 118, the second wall curving around a second wall axis 308 opposite the first wall axis 306 with respect to the major axis 116, the second wall axis 308 being parallel to the major axis 116, wherein the first wall 122 and the second wall 124 define a first cup portion x, as illustrated in FIG. 4, that has a first regular height $H_1$ measured from the base 120. FIG. 4 illustrates a side view of a tongue retractor, according to some embodiments. A second cup portion y has a gradually declining height measured from the base 120 in the distal direction.

In various embodiments, the tip 114 is bisected by the major plane 118. The tip 114, in some instances, curves away from the base 120 in a direction distal from the handle, the tip having a height $H_2$ measured from the base that is greater than the height of the second cup portion, and lesser than the height $H_1$ of the first cup portion. Embodiments in which the height $H_2$ is greater than the height $H_1$ are additionally contemplated. A first webbing 126 curving away from the base 120 and joins the first wall 122 and the tip 114, in some embodiments. In additional embodiments, a second webbing 128 curves away from the base 120 and joins the second wall 124 and the tip 114. In various embodiments, the base 120, first wall 122, the second wall 124, the tip 114, the first webbing 126 and the second webbing 128 define a concave cavity, with the junction between the base 120, the first wall 122, the second wall 124, the tip 114, the first webbing 126 and the second webbing 128 being curved.

The present subject matter comprises various materials, including, but not limited to, biocompatible embodiments of ultra high molecular weight polyethylene ("UHMWPE"), ultra low molecular weight polyethylene ("ULMWPE—PE-WAX"), high molecular weight polyethylene (HMWPE), high density polyethylene ("HDPE"), high density cross-linked polyethylene ("HDXLPE"), cross-linked polyethylene ("PEX"), medium density polyethylene ("MDPE"), low density polyethylene ("LDPE"), linear low density polyethylene ("LLDPE"), very low density polyethylene ("VLDPE"), polyamide such as Nylon®, polypropylene, polyvinylchloride, polystyrene including, but not limited to, high density polystyrene, polylactic acid, cellulose based products including, but not limited to wood, other plant based materials including starches such as carbohydrates, and biocompatible metal alloys such as stainless steel. Combinations of these and other materials are possible. Some embodiments mold a plastic handle to a stainless steel cup, and vice versa. Various embodiments are opaque. Additional embodiments are transparent or semi-transparent. Embodiments including tint are contemplated. Embodiments in which a cup is tinted one color, while a handle is tinted another color are contemplated. Various textures are contemplated including, but not limited to, gloss texture, matte texture, and other textures.

Figure 5:
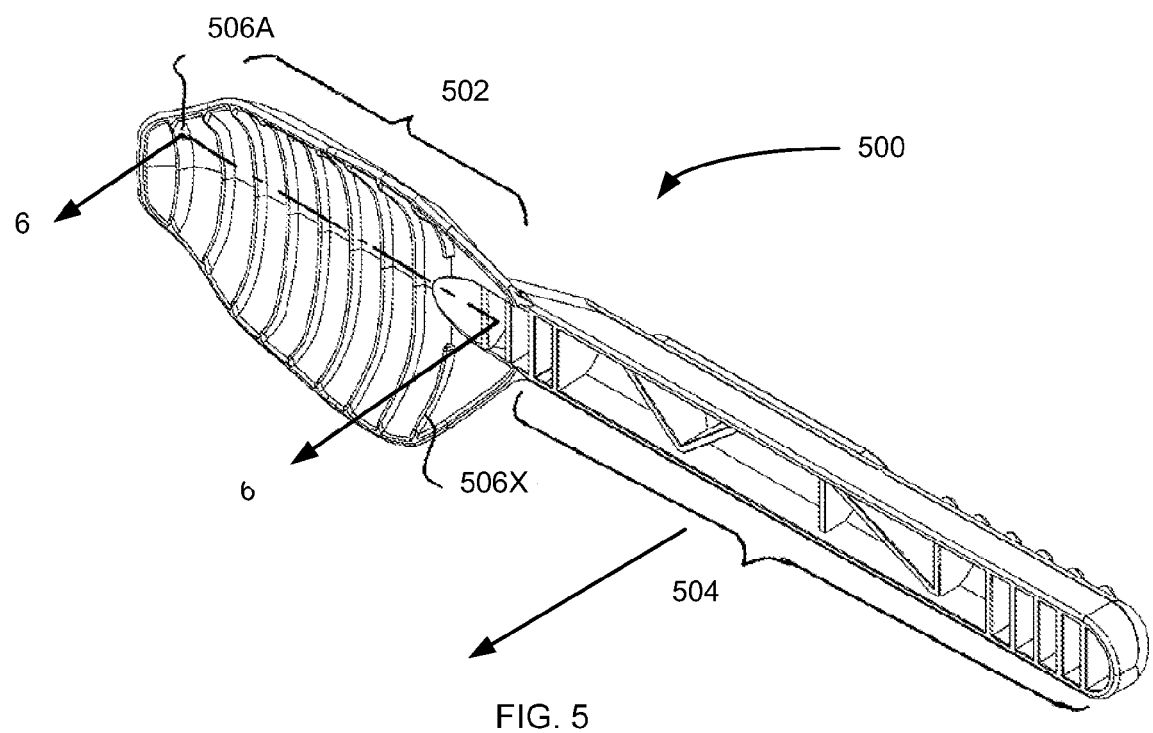
FIG. 5 illustrates a perspective view of a tongue retractor and cleaner, according to some embodiments.

FIG. 5 illustrates a perspective view of a tongue retractor and cleaner 500, according to some embodiments. The illustrated embodiment is for retracting at least a portion of the lateral sides of an animal tongue, at least a portion of the back of the animal tongue, and a dorsal portion of an animal tongue and for cleaning the animal tongue. The tongue retractor includes a cup 502 and a handle 504. The tongue retractor and cleaner additionally include means for cleaning the tongue coupled to the means for cupping the tongue. Cleaning means comprise any of the structures described herein that interrupt the continuity of the inner, concave side of the tongue cupping structures described herein. For example, the plurality of cleaning elements 506A-506X are coupled to the tongue receiving cup 102 extending away from the tongue receiving cup 102 and into the tongue receiving cavity. Embodiments that include a single cleaning element are contemplated.

Figure 6:
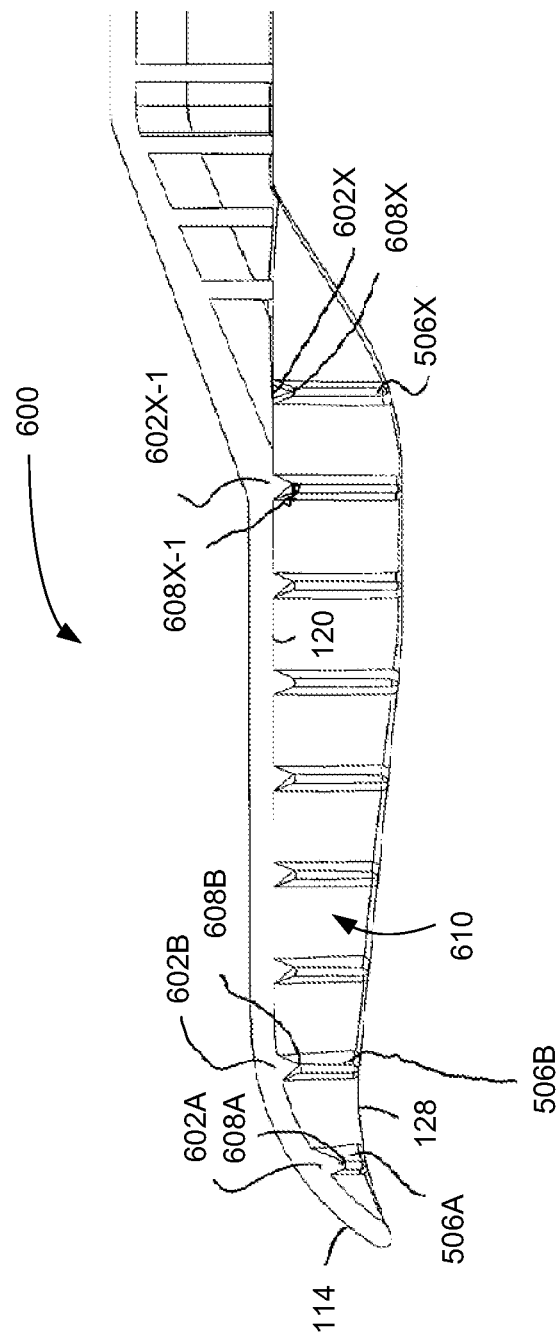
FIG. 6 illustrates a partial cross section of a tongue retractor an cleaner taken along line 6-6 in FIG. 5.

Various cleaning element shapes are contemplated. FIG. 6 illustrates a partial cross section of a tongue retractor and cleaner taken along line 6-6 in FIG. 5, FIG. 6 illustrates a tongue retracting and cleaning tool 600 including a plurality of cleaning elements 506A-506X, each having a generally triangular cross section, with a base 602A-602X of each triangular cross section coupled to the base 102 of the cup such than an apex 608A-608X of each triangle is disposed inside the concave cavity 610. In some examples, the cleaning elements have a triangular cross section along a cross section along an anterior posterior dorsal ventral plane, also known as a sagittal plane. In some instances, each triangular cross section of the plurality of cleaning elements defines respective isosceles triangles. Other embodiments define triangles having other shapes, including triangles that define an acute angle with respect to a base of a cup.

With reference to FIG. 4, the height of the cleaning elements crossing the base, the height measured from the base 120, is less than the height H1. This height is additionally less than the height of the second section in some examples. Further, this height is less than the height H2 in some examples. In various examples, the plurality of cleaning elements 506A-506X each are generally linear along a respective cleaning element axis, with each respective cleaning element axis being generally perpendicular to the major axis 116 as referred to in FIG. 1 of the handle 104. In additional examples, the cleaning elements have a semi-circular cross section along an anterior posterior dorsal ventral plane, also known as a sagittal plane, with the base of each cleaning element coupled to the tongue receiving cup 102. Some examples include cleaning elements that have a triangular cross section along the major plane 118. Some examples include plurality of cleaning elements coupled to the tip that are disposed in the tongue receiving cavity. In various examples, the plurality of cleaning elements each extend along the first wall, the second wall, and the base. Some of these examples include cleaning elements that additional extend along the tip.

Figure 7:
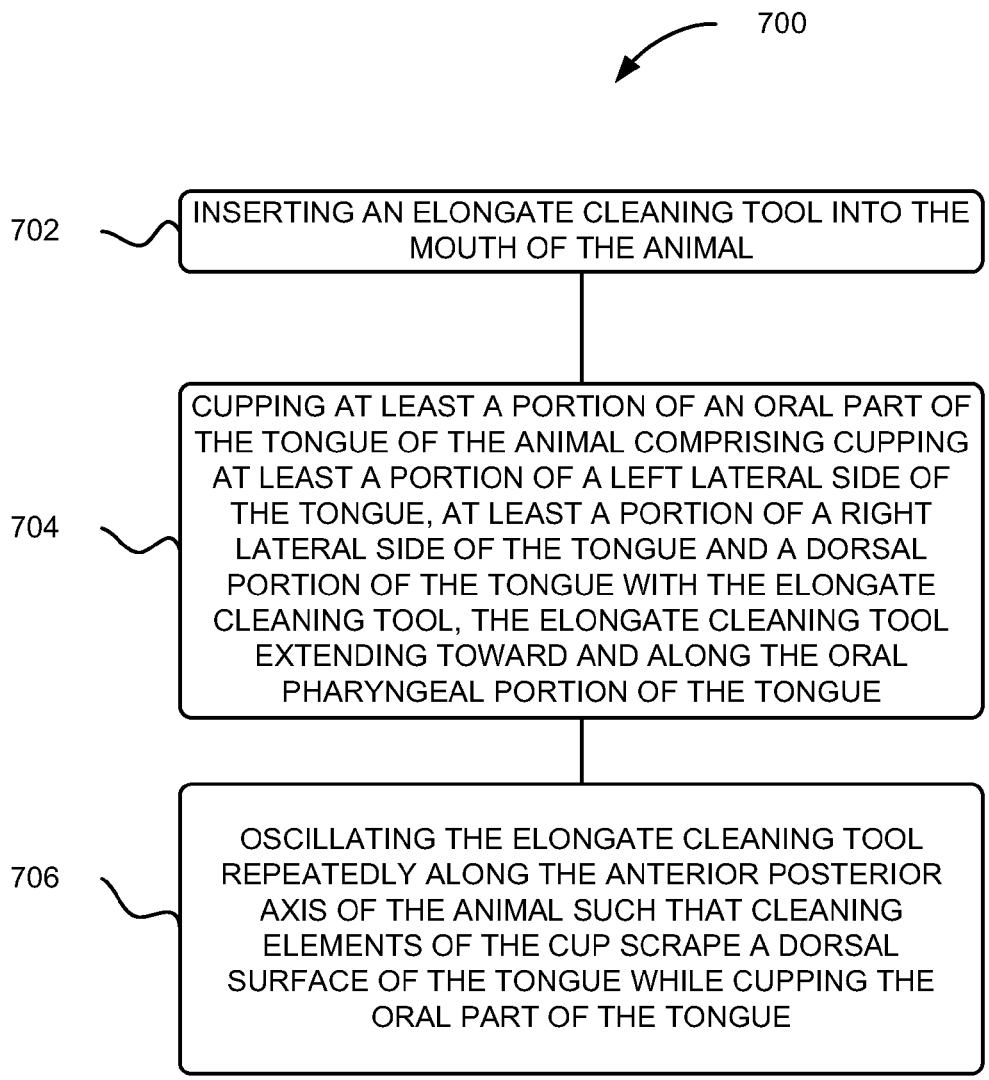
FIG. 7 illustrates a method of cleaning a tongue, according to some embodiments.

FIG. 7 illustrates a method 700 of cleaning a tongue, according to some embodiments. At 702, a method for cleaning an animal tongue includes inserting an elongate cleaning tool into the mouth of the animal. At 704, the method includes cupping at least a portion of an oral part of the tongue of the animal comprising cupping at least a portion of a left lateral side of the tongue, at least a portion of a right lateral side of the tongue and a dorsal portion of the tongue with the elongate cleaning tool, the elongate cleaning tool extending toward and along the oral pharyngeal portion of the tongue. In some embodiments, a tongue retractor is placed against the underside of the tongue, and extends around an oral frenulum of the patient. Example frenulums include the oral frenulum, an upper lip frenulum, or lower lip frenulum. The present subject matter is additionally useful to retract oral tissue proximal a lesion. In some examples, a lesion is straddled by a retractor such that the lesion is disposed in the relieve notch. In some examples, oral tissue is depressed and a tooth is disposed through the relief notch.

In some examples, oral tissue is protected by the retractor during a procedure such as a surgery. Example surgeries include, but are not limited to, laser surgeries. For example, tissues are covered by a retractor, with a surgery-target area such as a lesion exposed through the relief notch. During surgery, portions of the tissue are covered and protected from laser energy by the retractor and surgery-target areas are exposed through the relief notch. Accordingly, an operator is free to operate on the surgery-target area while reducing instances of undesirable damage to tissue not part of the surgery-target area.

At 706, the method includes oscillating the elongate cleaning tool repeatedly along the anterior posterior axis of the animal such that cleaning elements of the cup scrape a dorsal surface of the tongue while cupping the oral part of the tongue. Some methods include oscillating the elongate cleaning tool repeatedly along the anterior posterior axis of the animal such that the cleaning elements of the cup scrape the left lateral side of the tongue and the right lateral side of the tongue. Some methods include cupping the tongue of the animal with the elongate cleaning tool to reduce the potentiating of a pharyngeal ("gag") reflex. Optional methods include oscillating the elongate cleaning and retracting element without provoking a pharyngeal ("gag") reflex.

Figure 8:
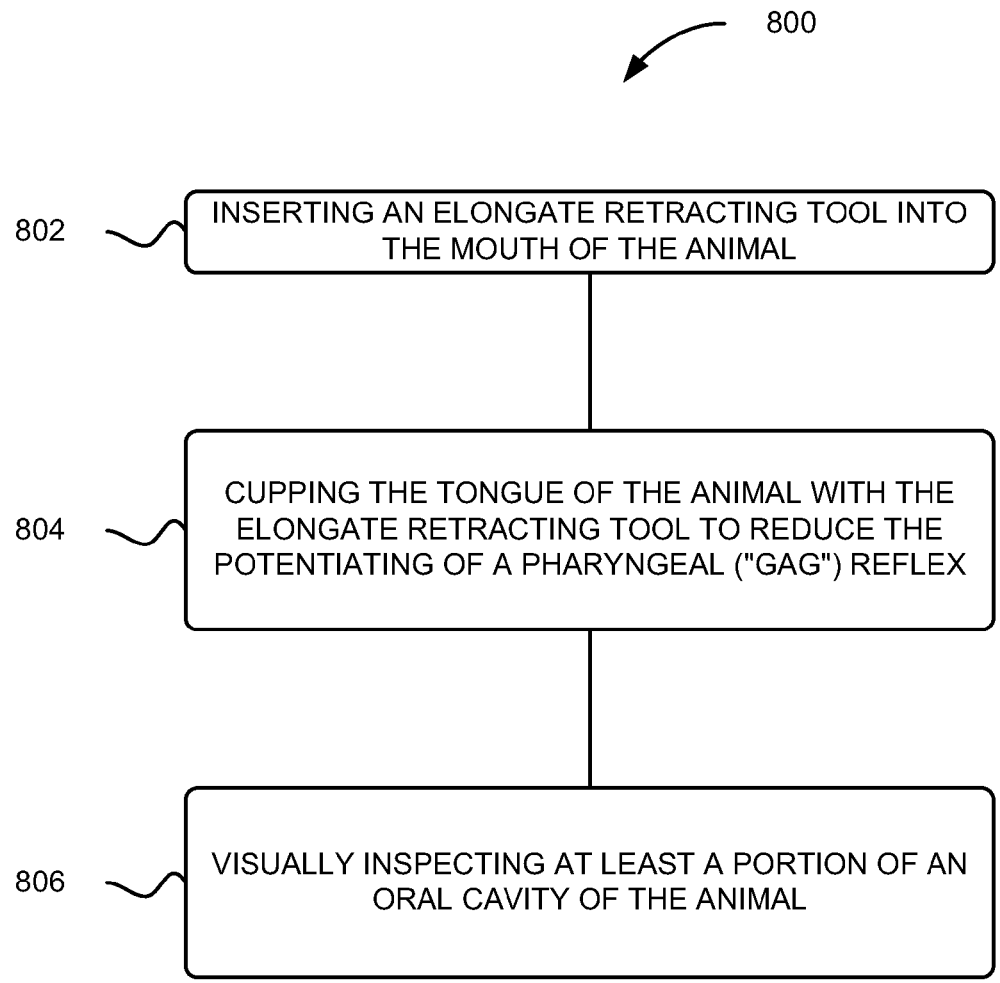
FIG. 8 illustrates a method of retracting a tongue, according to some embodiments.

FIG. 8 illustrates a method 800 of retracting a tongue, according to some embodiments. One method includes, at 802, inserting an elongate retracting tool into the mouth of the animal. At 804, the method includes cupping the tongue of the animal with the elongate retracting tool to reduce the potentiating of a pharyngeal ("gag") reflex. At 806, the method includes visually inspecting at least a portion of an oral cavity of the animal. Some methods include performing a dental procedure on the animal.

Some methods include cupping the tongue such that the tongue is substantially depressed in a ventral direction of the animal. Additional methods include cupping the tongue such that the tongue is substantially depressed in a lateral direction of the animal.

FIGS. 9A-E show a tongue retractor 900 with a relief notch, according to some embodiments. FIG. 10 is a cross sectioned view taken along line 10-10 in FIG. 9A. FIG. 11 is a sectioned close up view taken along section 11-11 in FIG. 10. These examples provide means for avoiding contact with the oral frenulum. In various embodiments, the receiving cup 902 defines a relief notch 910. In various embodiments, the relief notch 910 is sized to provide a relief for an oral frenulum when cupping a tongue from a position ventral or below the tongue, urging the tongue in a dorsal or upward direction. In various embodiments, the relief notch 910 is shaped to extend at least partially around the oral frenulum. In some examples, the relief notch 910 is shaped so that the receiving cup 902 can extend along two opposite sides of the oral frenulum. The shape of the relief is not limited to the shape shown in the example embodiment, and other shapes are possible, including slots, slits, parallelepiped openings, arcuate openings including the opening shown, and other openings.

The receiving cup 902 spans two sides of the underside of a tongue with a first side 912 and a second side 914. The distance the left side 912 and the right side 914 extend 914 posteriorly, i.e. their length, is illustrated as an example, and shorter or longer sides are possible. Some embodiments include only one side. Additional embodiments include two sides of different lengths. The posterior length of the relief notch 910 is additionally variable depending on the application for which the instrument is to be used. For example, longer notches are used for persons with longer oral frenulums, in certain examples.

Support beams 916 are illustrated and are formed as part of the tongue retractor 900 to improve the bending stiffness of the tongue retractor 900. The shape and configuration of these support beams is provided as an example only, and other shapes and/or numbers of support beams 916 are possible. Some examples of a tongue retractor do not include support beams 916.

In various examples the handle 920 is rigidly or stiffly coupled or fixed to the receiving cup 902. The rigid coupling resist bending while a tongue is retracted. In various embodiments, the rigid coupling is reinforced against bending, such that a hand force by an average man can retract the tongue with little or no bending between or of the handle 920 or receiving cup 902. As set forth herein, the handle 902 and receiving cup 902 are formed of materials and of a size to resist hand bending when used as a hand tool to retract a tongue.

Figure 9A:
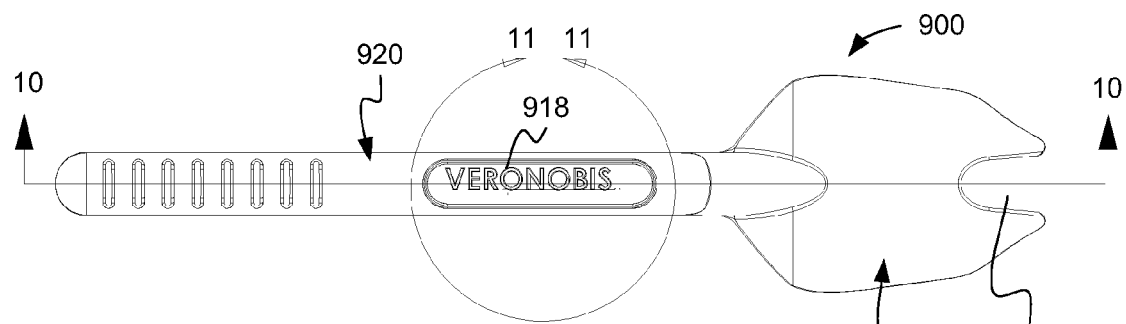
FIG. 9A illustrates a plan view of a tongue retractor with a relief notch, according to some embodiments.
Figure 9B:
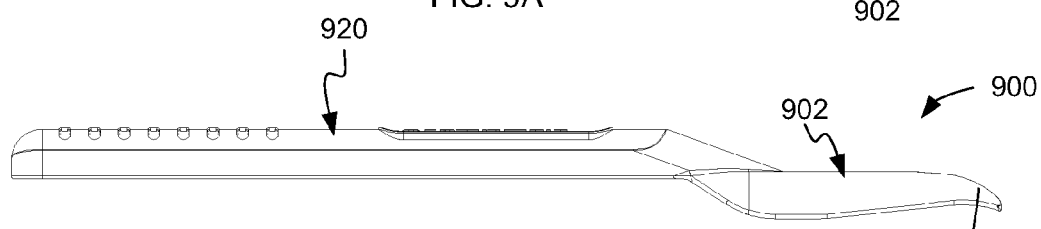
FIG. 9B illustrates a front view of the tongue retractor of FIG. 9A.
Figure 9C:
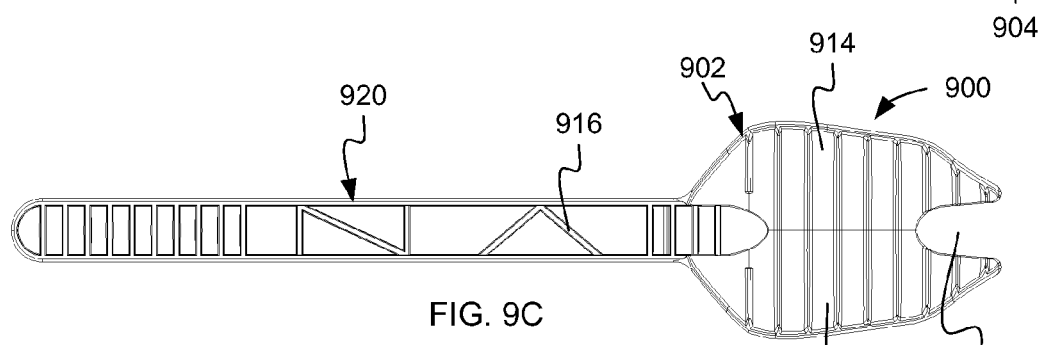
FIG. 9C illustrates a bottom view of the tongue retractor of FIG. 9A.
Figure 9D:
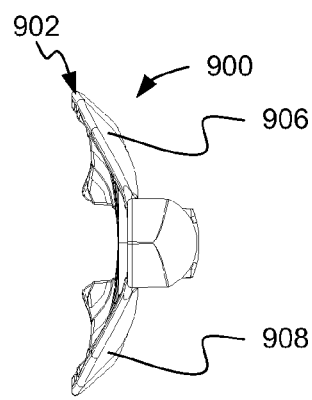
FIG. 9D illustrates a right side view of the tongue retractor of FIG. 9A.

FIG. 9B illustrates a front view of the tongue retractor of FIG. 9A. The tip 904 has a curvature to cup tissue. The present disclosure is not limited to tips having curvatures, and tips that are straight are also contemplated. FIG. 9D illustrates a right side view of the tongue retractor of FIG. 9A. Shows in a curved wall 906, opposite a further curved wall 908, with the two walls at least partially defining the receiving cup 902. The present subject matter is not limited to embodiments in which the walls 906 and 908 are curved, and other embodiments are possible. Combinations of flat walls, or no walls are possible. The present subject matter extends to tongue depressors in which a tongue depression portion, of which the receiving cup 902 is one species, have a tip and walls with no curvature, and depressors in which the tip has a curvature but the walls do not.

FIG. 12 is a sectioned view taken along section 12-12 in FIG. 9A, showing an indicia 918 optionally disposed on a tongue retractor, according to some embodiments. The term VERONOBIS is a common law trademark that may be federally registered, may be registered as a trademark in the state of New Hampshire, and that is provided as an example. Indicia 918 can define additional terms, shapes, icons or other indicia.

FIG. 13 is a sectioned view taken along section 13-13 in FIG. 12, showing an optional cleaning element 1302 disposed on a receiving cup of a tongue retractor, according to some embodiments. The cleaning element 1302 has generally triangular shape, with an apex 1304 that is optionally rounded. Some embodiments define a sharp apex. Some include a scraping edge that is squared. Other shapes are possible.

Among several embodiments, various numbers and shapes of cleaning element 1302 are possible. For example, some embodiments include fewer cleaning elements or no cleaning elements, while additional embodiments include cleaning elements that number in excess of the number shown in the above examples.

Figure 14:
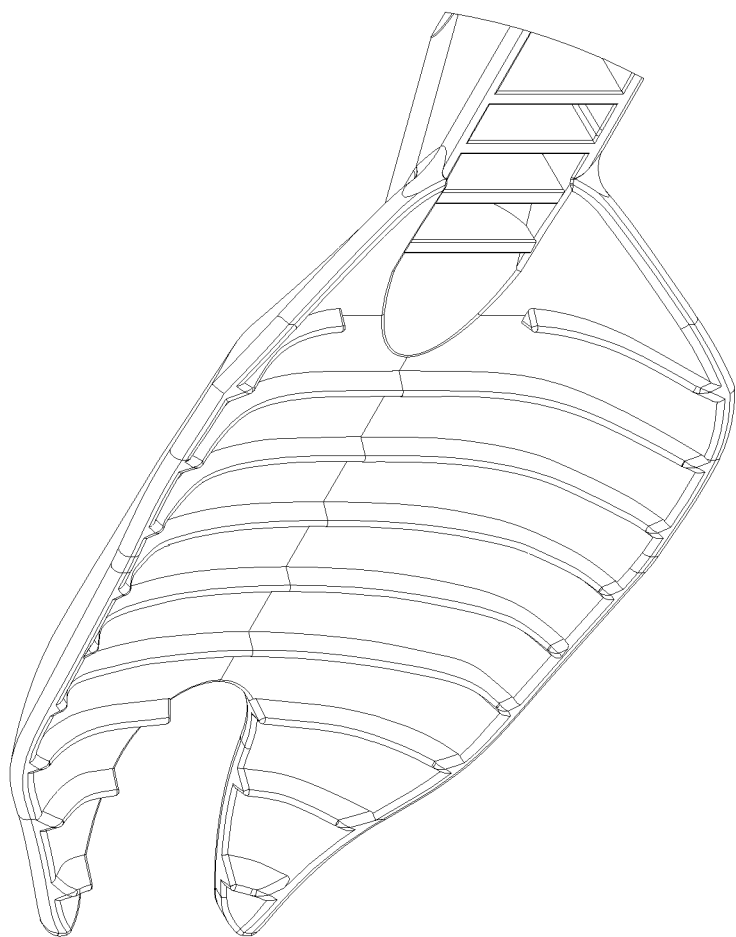
FIG. 14 is a sectioned view taken along section 14-14 in FIG. 9E, showing a relief notch optionally defined by a receiving cup of a tongue retractor, according to some embodiments.
Figure 9E:
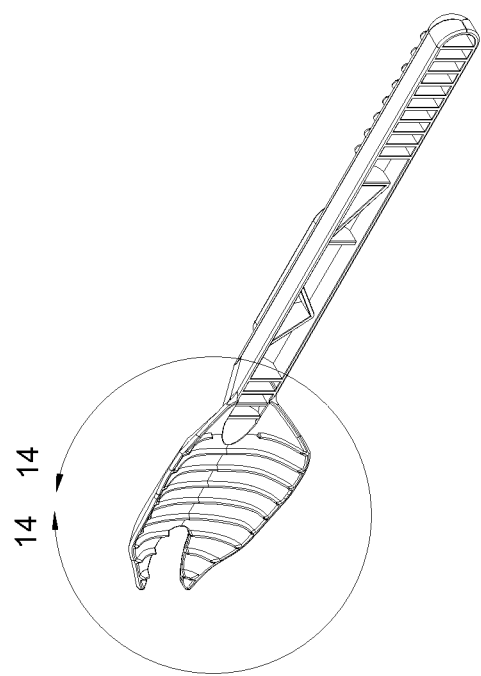
FIG. 9E illustrates a perspective view of the tongue retractor of FIG. 9A.

FIG. 14 is a sectioned view taken along section 14-14 in FIG. 9E, showing a relief notch optionally defined by a receiving cup of a tongue retractor, according to some embodiments.

Various methods of manufacture are contemplated, including injection molding the elongate cleaning and retracting tool. Some methods include modeling the animal tongue and rapid prototyping the elongate cleaning and retracting tool such that the cup form fits the tongue. Some embodiments disposed herein position a parting line such that the parting line is out of contact with tissue of the patient. For example, in some embodiments, the parting line is on a ventral surface of a tongue receiving cup, rather than being on the sides.

In some example methods, an operator such as an oral surgeon or an oncologist and displace a tongue using a tongue retractor such as the tongue retractor disclosed in FIGS. 9A-9E. The operator inserts the receiving cup of the tongue retractor under the tongue, with a concavity, if any, facing in a dorsal direction. In embodiments having a relief notch, such as a relief notch to provide clearance for an oral frenulum, two sides of the receiving cup that are on opposite sides of the notch are placed on the tongue on opposite sides of the oral frenulum. The operator can displace the tongue dorsally, but embodiments having a cup shape additionally enable the operator to displace the tongue laterally as well as in anterior and posterior directions, thus enabling the operator more control of tongue position.

Additionally, one or more of the devices and methods demonstrated herein are useful for ventral and lateral retraction of the tongue. The present subject matter demonstrates several benefits, such tongue retraction to expose various dental areas for oral procedures. Oral procedures include, but are not limited to, removal of foreign debris, dental examinations, surgeries, hygienist examinations, suturing, dental restoration, endodontic procedures, oral cancer screening examinations and any related intra-oral dental procedure.

During one or more of the procedures described here, in addition to other procedures, the present subject matter reduces the potentiating of a pharyngeal ("gag") reflex. The present subject matter disclosed herein can be used during collection of oral and throat culture specimens. In additional embodiments, it can be used during upper or hard palette procedures. Embodiments of the present subject matter can be used to retract oral cheek areas while performing oral procedures. For example, some embodiments enhance suctioning during oral procedures by providing for greater exposure of areas needed to be suctioned.

In some instances, the present subject matter is additionally useful for tongue cleaning and scraping to improve oral hygiene. Such embodiments can reduce halitosis. Some embodiments help reduce bacterial buildup on tongue surface. Embodiments disclosed herein provide for tongue scraping while reducing the potentiating of a pharyngeal ("gag") reflex. The present subject matter provides increased scraping and cleaning area by providing a plurality of cleaning elements, as disclosed herein.

Figure 15:
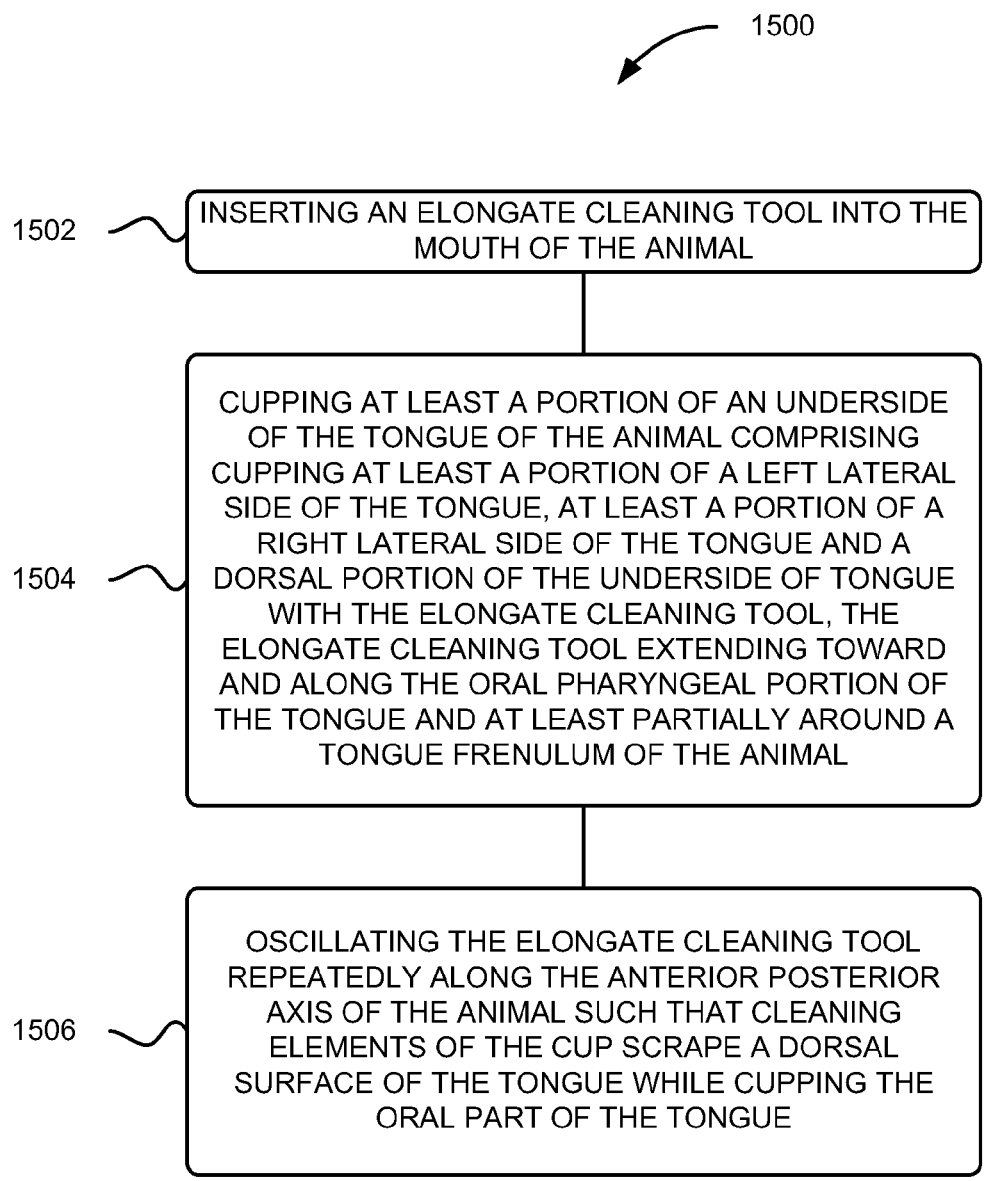
FIG. 15 illustrates a method of cleaning a tongue, according to some embodiments.

FIG. 15 illustrates a method 1500 of cleaning a tongue, according to some embodiments. At 1502, a method for cleaning an animal tongue includes inserting an elongate cleaning tool into the mouth of the animal. At 1504, the method includes cupping at least a portion of an underside of the tongue of the animal comprising cupping at least a portion of a left lateral side of the tongue, at least a portion of a right lateral side of the tongue and a dorsal portion of the underside of tongue with the elongate cleaning tool, the elongate cleaning tool extending toward and along the oral pharyngeal portion of the tongue and at least partially around an oral frenulum of the animal. In some embodiments, a tongue retractor is placed against the underside of the tongue, and extends around the oral frenulum of the patient.

At 1506, the method includes oscillating the elongate cleaning tool repeatedly along the anterior posterior axis of the animal such that cleaning elements of the cup scrape a dorsal surface of the tongue while cupping the oral part of the tongue. Some methods include oscillating the elongate cleaning tool repeatedly along the anterior posterior axis of the animal such that the cleaning elements of the cup scrape the left lateral side of the tongue and the right lateral side of the tongue. Some methods include cupping the tongue of the animal with the elongate cleaning tool to reduce the potentiating of a pharyngeal ("gag") reflex. Optional methods include oscillating the elongate cleaning and retracting element without provoking a pharyngeal ("gag") reflex.

Figure 16:
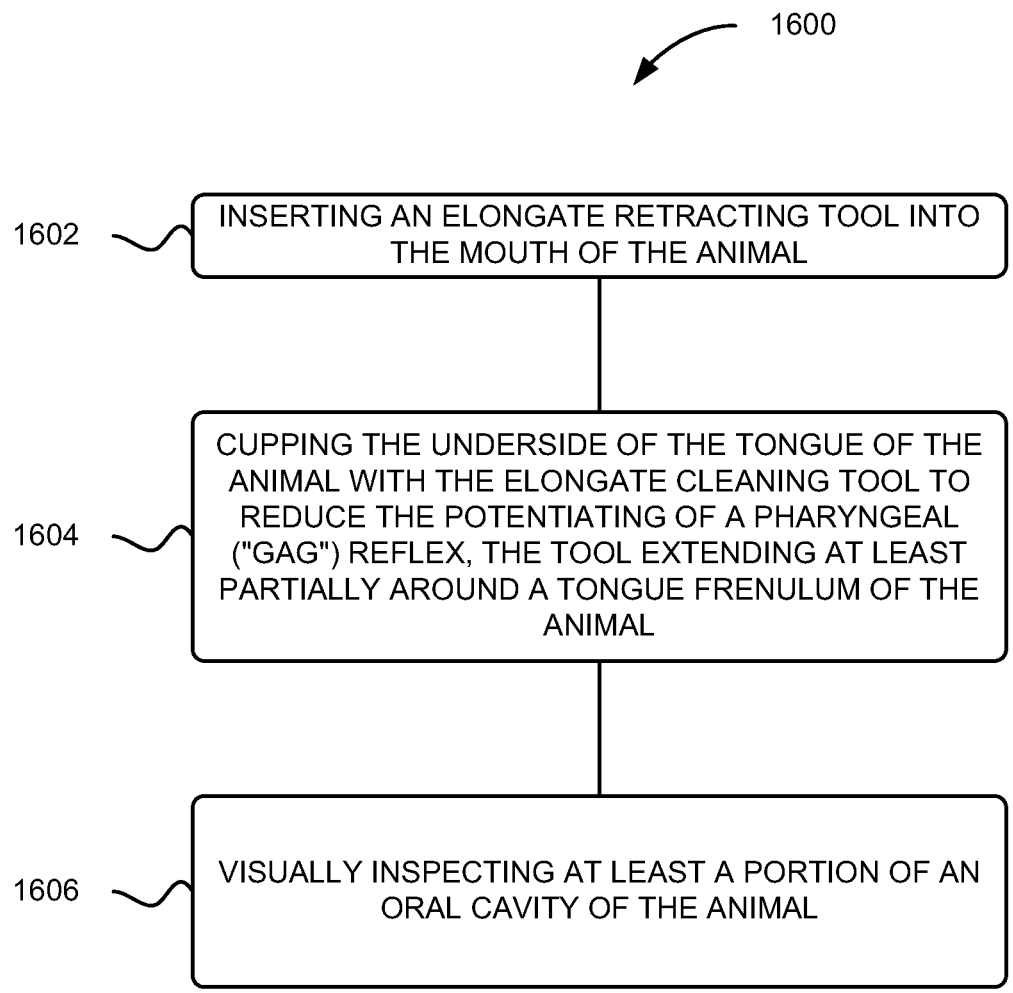
FIG. 16 illustrates a method of retracting a tongue, according to some embodiments.

FIG. 16 illustrates a method 1600 of retracting a tongue, according to some embodiments. One method includes, at 1602, inserting an elongate retracting tool into the mouth of the animal. At 1604, the method includes cupping the underside of the tongue of the animal with the elongate cleaning tool to reduce the potentiating of a pharyngeal ("gag") reflex, the tool extending at least partially around an oral frenulum of the animal. At 1606, the method includes visually inspecting at least a portion of an oral cavity of the animal. Some methods include performing a dental procedure on the animal.

Some methods include cupping the tongue such that the tongue is substantially depressed in a ventral direction of the animal. Additional methods include cupping the tongue such that the tongue is substantially depressed in a lateral direction of the animal.

It will be readily understood to those skilled in the art that various other changes in the details, material, and arrangements of the parts and method stages which have been described and illustrated in order to explain the nature of this invention may be made without departing from the principles and scope of the invention as expressed in the subjoined claims.

It is emphasized that the Abstract is provided to comply with 37 C.F.R. §1.72(b) requiring an Abstract that will allow the reader to quickly ascertain the nature and gist of the technical disclosure. It is submitted with the understanding that it will not be used to interpret or limit the scope or meaning of the claims.

What is claimed is:

1. An apparatus for retracting at least a portion of sides of an animal tongue, at least a portion of the back of the animal tongue, and a dorsal portion of an animal tongue, comprising:
   a tongue retraction handle that is elongate comprising a proximal portion that extends along a reference plane toward a distal portion, with the tongue retraction handle generally disposed above the reference plane; and
   a tongue retraction cup coupled to the distal portion of the tongue retraction handle, the tongue retraction cup extending along the reference plane and generally beneath the reference plane, the tongue retraction cup being generally concave and sized to position a first side of the tongue retraction cup at least partially over a first lateral side of the tongue, a second side opposite the first side at least partially over a second side of the tongue that is opposite the first lateral side of the tongue, a dorsal portion of the cup along the dorsal portion of the tongue and a posterior extending tip at least partially along the back of the tongue toward an oral pharyngeal portion of the tongue, the first side, second side, and posterior extending tip defining a tongue receiving cavity of the tongue retraction cup, wherein the tongue retraction cup defines a relief notch opening proximal the posterior extending tip, the relief notch sized to accommodate an oral frenulum,
   wherein the apparatus is formed of one or more materials adapted to maintain a shape, including an orientation of the tongue retraction handle with respect to the tongue retraction cup, to forcibly retract the animal tongue laterally.

2. The apparatus of claim 1, wherein the apparatus is for cleaning the animal tongue, and further comprising cleaning elements coupled to the tongue retraction cup and extending away from the tongue retraction cup and into the tongue receiving cavity.

3. The apparatus of claim 1, wherein a cross section of the cup at a left right dorsal ventral plane has a form factor that substantially matches a cross section of the tongue at the left right dorsal ventral plane.

4. The apparatus of claim 1, wherein a cross section of the cup at an anterior posterior dorsal ventral plane has a form factor that substantially matches a cross section of the tongue at the anterior posterior dorsal ventral plane.

5. The apparatus of claim 1, wherein the tongue retraction cup comprises polyethylene.

6. The apparatus of claim 5, wherein the tongue retraction cup comprises high density polyethylene.

7. The apparatus of claim 1, wherein the tongue retraction cup comprises polyamide.

8. The apparatus of claim 1, wherein the tongue retraction cup comprises polypropylene.

9. The apparatus of claim 1, wherein the tongue retraction cup comprises cellulose.

10. The apparatus of claim 1, wherein the animal is a human.

11. An apparatus for retracting at least a portion of sides of an animal tongue, at least a portion of the back of the tongue, and a dorsal portion of the animal tongue, comprising:
    a tongue retraction handle that is elongate and comprises a proximal portion that extends along a reference plane toward a distal portion, with the tongue retraction handle generally disposed above the reference plane; and
    means for cupping an underside of the tongue coupled to the distal portion of the handle, the means for cupping additionally for avoiding contact with an oral frenulum of the animal, the means for cupping extending along the reference plane and generally beneath the reference plane,
    wherein the apparatus is formed of one or more materials adapted to maintain a shape, including an orientation of the tongue retraction handle with respect to the means for cupping, to forcibly retract the animal tongue laterally.

12. The apparatus of claim 11, wherein the means for cupping the tongue of the animal comprise means for cupping the tongue by cupping an oral portion of the tongue and by at least partially cupping the oral pharyngeal portion of the tongue.

13. The apparatus of claim 11, wherein the apparatus for retracting at least a portion of sides of an animal tongue, at least a portion of the back of the tongue, and a dorsal portion of the animal tongue is for cleaning the animal tongue and further comprising means for cleaning the tongue coupled to the means for cupping the tongue.

* * * * *

UNITED STATES PATENT AND TRADEMARK OFFICE
CERTIFICATE OF CORRECTION

| | | |
|---|---|---|
| PATENT NO. | : 8,740,788 B1 | Page 1 of 1 |
| APPLICATION NO. | : 12/794686 | |
| DATED | : June 3, 2014 | |
| INVENTOR(S) | : Mettler, Jr. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 724 days.

Signed and Sealed this
Eleventh Day of August, 2015

Michelle K. Lee
*Director of the United States Patent and Trademark Office*